United States Patent

Brown et al.

[11] Patent Number: 6,022,552
[45] Date of Patent: Feb. 8, 2000

[54] UNIFORM MIXTURES OF PESTICIDAL GRANULES

[75] Inventors: Philip Alexander Brown; Luann Marshall Pugh, both of Wilmington, Del.

[73] Assignee: E. I. du Pont de Nemours and Company, Wilmington, Del.

[21] Appl. No.: 08/981,202

[22] PCT Filed: Jun. 19, 1996

[86] PCT No.: PCT/US96/10581

§ 371 Date: Dec. 18, 1997

§ 102(e) Date: Dec. 18, 1997

[87] PCT Pub. No.: WO97/00608

PCT Pub. Date: Jan. 9, 1997

Related U.S. Application Data

[63] Continuation-in-part of application No. 08/494,641, Jun. 23, 1995, abandoned.

[51] Int. Cl.[7] .................................................. A01N 25/08

[52] U.S. Cl. ........................... 424/408; 424/409; 424/410; 424/412; 424/489

[58] Field of Search ...................... 424/405, 408, 424/409, 410, 438, 464, 465, 489, 84, 412

[56] References Cited

U.S. PATENT DOCUMENTS

| | | | |
|---|---|---|---|
| 2,936,263 | 5/1960 | Hardt et al. | 167/55 |
| 3,089,824 | 5/1963 | Wyrster | 167/82 |
| 3,892,905 | 7/1975 | Albert | 428/220 |
| 3,920,442 | 11/1975 | Albert et al. | 71/92 |
| 4,626,534 | 12/1986 | Fiter et al. | 514/203 |
| 4,943,307 | 7/1990 | Petre et al. | 71/3 |

*Primary Examiner*—Neil S. Levy

[57] ABSTRACT

A homogeneous mixture of solid granules cylindrical in shape of one or more groups which have substantially uniform diameters and a longitudinal length of no more than eight times the diameter with the average length being 1.5 to 4 times the diameter and wherein the diameters vary from one group to another by no more than 30%.

10 Claims, No Drawings

UNIFORM MIXTURES OF PESTICIDAL GRANULES

This application is a continuation-in-part of application Ser. No. 08/494,641 filed Jun. 23, 1995, now abandoned.

BACKGROUND OF THE INVENTION

The present invention relates to blends of pesticidal granules in various cylindrical shapes that are nonsegregating.

Pesticidal granules that are water-dispersible granules disintegrate in spray tank water to form a fine dispersion of primary particles, which then can be applied to crops by spraying. Pesticidal granules can also be totally water soluble. Pesticidal granules can also be applied dry.

In agriculture, more than one pesticide is often needed to treat a particular crop. In such a case, granules can be prepared which contain a combination of pesticides or alternatively separate granules prepared for each pesticide. It is desirable to apply a combination of pesticides simultaneously in one pass when spraying crops rather than making separate passes over the field with each pesticide.

In the use of two or more water dispersible granules each granule is added to the same spray tank whereupon they disintegrate and become homogeneous in water which can be sprayed on to the crop. However, adding individual pesticides to the spray tank is not entirely satisfactory because it is inconvenient to have to measure out separate products and there is increased risk of mismeasurement. A single product containing all the necessary pesticides is preferred.

Pesticide mixture products in which each granule contains more than one pesticide are commercially available. However, for various markets, the pesticides are needed in different combinations and ratios. This proliferates the number of products and leads to complicated manufacturing and stockage issues. It would be advantageous to produce pesticide granules with a single active ingredient which can be combined with a different granular pesticide to form a mixture of granules in the desired ratio as a physical mixture before addition to a spray tank.

Physical mixtures of individual granules of mismatched sizes present a risk of segregation and therefore misapplication when dispensed in part. One solution to the segregation problem as regards water dispersible granules is to package the mixture as a "unit pack" where the entire content of the package is used in the spray tank. An example of a unit pack is a water-soluble bag which is simply tossed into a spray tank full of water whereupon the bag dissolves releasing the contents. Another example of a unit package is a bottle containing only one dose.

Although the unit package is one method to address the problems associated with granule mixtures, such a package lacks flexibility in dosage as the entire contents of the package must be emptied at once.

Most water dispersible granules currently produced are "isodimensional", meaning they are approximately spherical and are produced by granulation methods such as fluid bed, pan or disc, high shear, spray drying and the like, and also paste extrusion wherein the extrudate is post treated to give an isodimensional shape (e.g., WO 89/00079). Granules produced by these methods tend to have a high variability in granule size distribution but can be sized by sieving. To maximize productivity, the product size range is as broad as possible and granules outside the desired product size distribution can be recycled or reworked. Even with the same process equipment, there tends to be batch to batch and product to product variations in size distribution of granules.

It has been suggested in FR 2,704387 that to obtain a nonsegregating mixture of granules, the ratio of median diameters of two categories of granules must be 10 or less. The normal product size distribution of the disclosed granulation techniques typically fall within that range. However, to achieve the preferred ratio of 2 or less, extensive post production separation of the granules is required. Data shows that even when the diameter ratio is less than 2, significant inhomogeneity can result from size segregation. It would be advantageous for a normal product size distribution to be suitable for admixture into nonsegregating mixtures without further size separation.

SUMMARY OF THE INVENTION

The present invention pertains to mixtures of pesticidal granules that remain homogenous when stored, handled and dispensed. It has been found that homogenous blends of granules result when mixing different granules of substantially similar size and shape. Such mixtures that remain homogenous make it possible to dispense the contents in part and provide a reproducible composition.

The granules of the present invention have a similar size and are characterized as substantially cylindrical in shape. What is meant by substantially cylindrical is rod like or tubular wherein the cross-sectional shape may be circular, octagonal, rectangular, or any other conceivable shape and wherein the longitudinal surface is spiral, curved, or straight. The longitudinal length of the substantially cylindrical granules of the invention is no more than eight (8) times the diameter (cross-sectional width at it's widest point) preferably 1 to 4 times the diameter with the average length being 1.5 to 4.0 times the diameter.

The diameters of the cylindrical granules in admixture have a significant effect on granule segregation and uniformity. Advantageously, techniques for manufacture of the cylindrical granules by extrusion provide a high degree of control of granule diameter therefore permitting the matching of the diameters of the cylindrical granules in the normal course of production. There is no need for extensive post production size separation.

Containers of the cylindrical granule mixtures of the present invention therefore can be made up of two or more different pesticidal granules and provide a nonsegragating composition. The granules can be water-dispersible, water-soluble, and/or nondispersible. Accordingly, a homogeneous mixture of solid granules has been discovered comprising granules cylindrical in shape having a diameter that differs from one group of the mixture to another group by no more than 30% with longitudinal lengths of no more than eight (8) times the diameter with the average length being 1.5 to 4.0 times the diameter.

Thus, the present invention is directed to mixtures of pesticidal granules comprising cylindrically shaped granules wherein one group of the mixture has one pesticide or pesticide content with a longitudinal length no more than eight (8) times the diameter with the average length being 1.5 to 4.0 times the diameter and one or more other groups having another pesticide or inert content with a longitudinal length no more than eight (8) times the diameter with the average length being 1.5 to 4.0 times the diameter, the diameter of each group differing from another group by no more than 30%.

DETAILS OF THE INVENTION

In accord with the present invention, the pesticidal granules of the invention can comprise a blend of at least two sets of granules which differ in diameter by 0 to 30%, and have the required longitudinal length. One set of granules can contain pesticide, the other set(s) of granules can contain no pesticide or a different pesticide and additionally, for example, adjuvant(s). Pesticides refers to agriculturally active ingredients such as herbicides, fungicides, bactericides, insecticides, insect antifeedants, acaricides, miticides, nematocides, and plant growth regulants.

Further in accord with the present invention there is provided a mixture of the granules of the invention which can be containerized in other than a unit package and be flexibly dosed in two or more uniform portions. The "container" refers to the container in which the granule mixture is provided to the customer, and includes the containers typically used for this purpose such as bottles, bags and the like. However, even though not required the granule mixture of this invention could also be packaged in unit doses. By unit dose is meant an amount of the mixture of the invention to be added to a water spray tank. The packaging could be in the case of unit doses a water soluble polymer. The water soluble polymer may be selected from polyethylene oxide, methylcellulose and polyvinyl alcohol with polyvinyl alcohol being the preferred polymer.

By uniform portions it is meant that the mixture will not vary in pesticide assay beyond a range that is acceptable to the regulatory agencies which carefully scrutinize agricultural compositions. It is important to recognize that the variability in a measurement of a physical mixture of granules is inversely proportional to the sample size taken. However, the acceptable variation in a sample composition can be as high as 10–15% depending on absolute composition. Generally the pesticide assay of each portion of the mixture constituting the invention will be within ±5%, preferably ±3%, of the product's labeled composition.

Sources of assay variability include the uncertainty in the assay method itself. For granular mixtures, assay variability is increased when there are granules with a wide size distribution beyond the limits of the present invention.

Cylindrical granules result from granulation techniques such as extrusion and pelletization. These techniques provide granules that are very consistent in size and shape. For conventional paste extrusion, the diameter is controlled (by choice of die) but the longitudinal lengths are determined by breaking of extruded strands in a drying step or post drying step. For other pelletization and extrusion techniques, both diameter and length can be precisely controlled. Extrusion and pelletization techniques can produce cylindrical granules which are consistent in size from batch-to-batch and even product-to-product.

Because of their shape, cylindrical granules cannot be readily classified by traditional sieving. However generally the extrusion process for forming cylindrical shaped granules of the invention can produce substantial uniform longitudinal lengths. Generally weighted average lengths of 1.5 to 4 times the diameter contain lengths that may vary up to 8 times the diameter.

It has been found that the diameter of the cylindrical granules has an effect on blend homogeneity. The average diameter of the largest granules in the mixture is no more than about 30% larger than the average diameter of the smallest granules in the mixture. More preferably the average diameter of the largest diameter granules in the mixture is no more than about 20% larger than the average diameter of the smallest diameter granules in the mixture. Most preferably the average diameters of all cylindrical granules differ by 0–10%. The absolute diameter of the cylindrical granules can be any suitable diameter, generally though the diameter is in the range of 0.4 to 10 mm and more typically in the range of 0.8 to 2 mm.

In addition, differences in length can also effect homogeneity of cylindrical granules. The length of the cylindrical pesticidal granules of the present invention are 1 to 8 times the diameter. Preferably, the length of the granules are 1 to 4 times the diameter.

Although the preceding discussion focused on water dispersible granules, it will be appreciated that the preceding applies to non-dispersible granules.

Examples of suitable pesticides can include, but are not limited to the following: herbicides such as acifluorfen, asulam, atrazine, azafenidin, bensulfuron methyl, bentazon, bromacil, bromoxynil, hydroxybenzonitrile, chloramben, chlorimuron ethyl, chloroxuron, chlorsulfuron, chlortoluron, cyanazine, dazomet, desmediphan, dicamba, dichlorbenil, dichlorprop, diphenamid, dipropetryn, diuron, thiameturon, fenac, fenuron, fluometuron, fluridone, fomesafen, glyphosate, hexazinone, imazamethabenz, imazaquin, imazethapyr, ioxynil, isoproturon, isouron, isoxaben, karbutilate, lenacil, MCPA, MCPB, mefenacet, mefluidide, methabenzthiauron, methazole, metribuzin, metsulfuron methyl, monuron, naptalam, neburon, nitralin, norflurazon, oryzalin, perfluidone, phenmedipham, picloram, prometryn, pronamide, propanil, propazine, pyrazon, rimsulfiron, siduron, simazine, sulfentrazone, sodium 2-chloro-6-(4,6-dimethoxy pyrimidine-2-ylthio)benzoate, sulfometuron methyl, tebuthiuron, terbacil, terbuthylazine, terbutryn, thifensulfuron methyl, triclopyr, 2,4-D, 2,4-DB, triasulfuron, tribenuron methyl, triflusulfuron methyl, primisulfuron, pyrazosulfuron ethyl, nicosulfuron, ethametsulfuron methyl, 2-[2,4-dichloro-5-[(2-propynyl)oxy]phenyl-5,6,7,8-tetrahydro-1,2,4-triazolo-[4,3-a]-pyridin-3-(H)-one, methyl 2-[[[[(4,6-dimethoxy-2-pyrimdinyl)amio]carbonyl]amino]sulfonyl]-6-(trifluoromethyl)-3-pyridinecarboxylate sodium salt, N-[(4,6-dimethoxypyrimidin-2-yl)aminocarbonyl]-1-methyl-4-(2-methyl-2H-tetrazol-5-yl)-1H-pyrazole-5-sulfonamide and N-[(4,6diethoxypyrimidin-2-yl)aminocarbonyl]-1-methyl-4-ethoxycarbonyl-5-pyrazolesulfonamide; fungicides such as carbendazim, thiuram, dodine, chloroneb, captan, famoxadone, folpet, thiophanatemethyl, thiabendazole, chlorothalonil, dichloran, captafol, iprodione, vinclozolin, kasugamycin, triadimenol, flutriafol, flusilazol, hexaconazole, and fenarimol; bactericides such as oxytetracycline dihydrate; acaricides such as hexathizox, oxythioquinox, dienochlor, and cyhexatin; and insecticides such as carbofuran, carbaryl, methyl 7-chloro-2,5-dihydro-2-[[methoxycarbonyl)4-(trifluoromethoxy)phenylamino)-carbonyl]inden-(1,2-E)(1,3,4)oxadiazine-4A-carboxylate thiodicarb, deltamethrin, and tetrachlorvinphos.

Especially preferred are the sulfonylurea herbicides which is meant to include the entire class of herbicides containing the following and any closely related chemical functionalities:

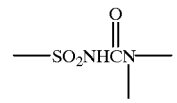

In accord with the present invention, there is provided a mixture of pesticidal granules which can be uniformly dosed thereby allowing easy preparation of a broad range of blend ratios to satisfy different markets and thus solving many manufacturing and inventory problems. Furthermore, the normal product size distribution of granules can be used "as made" without need for substantial postproduction size separation.

The following examples are intended to illustrate but not limit the present invention.

EXAMPLE 1

Effect of Cylindrical Granule Diameter on Segregation

Two 50/50 blends of cylindrical granules A and B were made wherein the diameter of the granules was varied. The granules were prepared by paste extrusion using a bench top basket extruder, and the resulting extrudate was dried in a fluid bed drier. The motion of the granules in the dryer provided the mechanism for the extrudate to break into smaller lengths, the average length of the granules were 2–3 times the diameter or cross-sectional width. In each experiment, 50 g of granules containing about 50% pesticide was blended with 50 g of Placebo granules containing no pesticide. The mixture was put into a polyethylene bottle which was inverted until visually homogeneous and thereafter shaken on a mechanical shaker for 15 minutes. The mixture was then poured continuously into ten aliquots of 10 g each. Each aliquot was homogenized by grinding into a powder and assayed for pesticide by standard HPLC techniques. The results are summarized below using relative standard deviation (Relative Standard Deviation is the standard deviation divided by percent pesticide times 100) as a means to compare our data variation to what would be accepted by regulatory agencies (generally 3–5%).

|  | A | B |
| --- | --- | --- |
| Active Granules |  |  |
| Diameter (mm) | 1.0 | 1.2 |
| Average Length (mm) | 2.1 | 2.5 |
| Placebo Granules |  |  |
| Diameter (mm) | 1.0 | 1.0 |
| Average Length (mm) | 2.1 | 2.1 |
| Diameter difference (%) | 0 | 20 |
| % Pesticide (Average of 10 aliquots) | 26.3 | 26.1 |
| Relative Standard Deviation (%) | 2.0 | 3.3 |

EXAMPLE 2

Effect of Cylindrical Granule Length on Segregation

For this example, actual pesticidal granules in discrete lengths were not readily available so instead, cylindrical plastic beads in different colors were used, as follows.

|  | Black | Silver | Gold | Pink |
| --- | --- | --- | --- | --- |
| Diameter (mm) | 2.0 | 2.0 | 2.0 | 2.0 |
| Length (mm) | 6.4 | 5.0 | 5.0 | 3.2 |
| Beads/gram | 26 | 33 | 33 | 50 |

The beads, of same diameter and different lengths, were mixed in 200 gram batches, bottled and shaken as in Example 1 and then poured out in five aliquots of 40 grams. Each aliquot was "assayed" by manually separating the beads by color and measuring the total weight of each color. The results were as follows.

| Mixture Composition | Relative Standard Deviation |
| --- | --- |
| 50% Silver + 50% Gold | 3.7% |
| 50% Pink + 50% Black | 5.3% |
| 50% Silver + 50% Black | 2.3% |

The relative lengths varied from 1:1 for the silver+gold beads to 2:1 for the pink+black beads. There was good homogeneity of the plastic beads.

COMPARATIVE EXAMPLE A

Illustration of a Mixture of Isodimensional Granules

Two 50/50 mixtures of isodimensional granules, A and B, were made wherein the relative average diameter (mesh size) of the each set of granules was varied. In each case, 50 g of active granules containing about 50% pesticide was blended with 50 g of Placebo granules containing no pesticide. The mixture was put into a polyethylene bottle which was inverted until visually homogeneous, then shaken on a mechanical shaker for 15 minutes. The mixture was then poured continuously into ten aliquots of 10 g each. Each aliquot was homogenized by grinding into a powder and analyzed for assay by standard HPLC techniques. The results are summarized below.

|  | A | B |
| --- | --- | --- |
| Active Granules |  |  |
| Mesh Size | −25/+30 | −14/+60 |
| Placebo Granules |  |  |
| Mesh Size | −35/+40 | −14/+60 |
| Diameter Ratio | 1.7 | 5.6 |
| Diameter Difference (%) | 70 | 460 |
| % Pesticide (Average of 10 aliquots) | 23.9 | 23.5 |
| Relative Standard Deviation (%) | 16.6 | 13.6 |

The granules in this example were fluid bed granulated. It can be seen that it is very difficult to match these granules in a mixture which can be uniformly dosed.

The 14/60 mesh size is a typical product cut for commercial pesticide granules. However, within that range, the distribution of granules sizes can vary from product-to-product and batch-to-batch. So even for mixtures of granules having the same nominal size distribution, as in mixture B, there can be substantial nonuniformity in the dosing. The breakdown in mesh size with the 14/60 mesh product distribution is a follows:

| Mesh Size | % in Active | % in Placebo |
| --- | --- | --- |
| 14–30 | 53 | 36 |
| 30–40 | 29 | 28 |
| 40–50 | 14 | 25 |
| 50–60 | 3 | 10 |

The distribution of sizes within the 14/60 mesh range reflect the distribution "as made". The distribution was not deliberately adulterated. Other granulation techniques for making isodimensional granules give similarly broad size ranges which also vary in distribution within the product size range from batch-to-batch and product-to-product.

COMPARATIVE EXAMPLE B
Effect of Cylindrical Granule Diameter on Segregation

A 50/50 blend of cylindrical granules was made wherein the relative diameter of the granules was varied. The granules were prepared by paste extrusion using a bench top basket extruder, and the resulting extrudate was dried in a fluid bed drier. The motion of the granules in the dryer provided the mechanism for the extrudate to break into smaller lengths, the average length of the granules were 2–3 times the diameter or cross-sectional width. In this experiment, 50 g of granules containing about 50% pesticide was blended with 50 g of Placebo granules containing no pesticide. The mixture was put into a polyethylene bottle which was inverted until visually homogeneous and thereafter shaken on a mechanical shaker for 15 minutes. The mixture was then poured continuously into ten aliquots of 10 g each. Each aliquot was homogenized by grinding into a powder and assayed for pesticide by standard HPLC techniques. The results are summarized below.

| Active Granules | |
|---|---|
| Diameter | 1.2 |
| Average Length | 2.5 |
| Placebo Granules | |
| Diameter | 0.8 |
| Average Length | 2.5 |
| Diameter difference (%) | 50 |
| % Pesticide (Average of 10 aliquots) | 26.0 |
| Relative Standard Deviation % | 10.6 |

We claim:

1. A homogeneous mixture, comprising two or more groups of solid pesticidal granules, wherein one group has one pesticide or pesticide content and one or more other groups have a different pesticide, a different pesticide content or an inert content, the granules within each group being formed by extrusion or pelletization and being substantially cylindrical in shape, having substantially uniform diameters, and longitudinal lengths 1 to 8 times the diameter with the average length of the granules being 1.5 to 4 times the diameter, and the average diameter of each group differing from another group by no more than 30%.

2. The mixture of claim 1 wherein the longitudinal length of each group is from 1.5 to 4 times the diameter of the granules.

3. The mixture of claim 1 wherein the diameter of the granules differ from one group to any other in the mixture by no more than 20%.

4. The mixture of claim 1 wherein the diameter of the granules differ from one group to any other in the mixture by no more than 10%.

5. The mixture of claim 2 wherein the diameter of the granules differ from one group to any other in the mixture by no more than 20%.

6. The mixture of claim 2 wherein the diameter of the granules differ from one group to any other in the mixture by no more than 10%.

7. The mixture as in any of the preceding claims containerized in a unit dosed package.

8. The mixture of claim 7 wherein the package is a water soluble polymer.

9. The mixture of claim 8 wherein the water soluble polymer is selected from polyethylene oxide, methylcellulose and polyvinyl alcohol.

10. The mixture of claim 9 wherein the water soluble polymer is polyvinyl alcohol.

* * * * *